(12) United States Patent
Yoshida

(10) Patent No.: US 11,925,490 B2
(45) Date of Patent: *Mar. 12, 2024

(54) PACKAGED MEDICAL DEVICE

(71) Applicant: DAIKYO SEIKO, LTD., Tochigi (JP)

(72) Inventor: Takayuki Yoshida, Tochigi (JP)

(73) Assignee: DAIKYO SEIKO, LTD., Tochigi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/077,316

(22) Filed: Dec. 8, 2022

(65) Prior Publication Data

US 2023/0096169 A1    Mar. 30, 2023

Related U.S. Application Data

(63) Continuation of application No. 16/493,395, filed on Sep. 12, 2019, now Pat. No. 11,547,518.

(51) Int. Cl.
*A61B 50/30* (2016.01)
*A61B 50/00* (2016.01)

(52) U.S. Cl.
CPC ........ *A61B 50/30* (2016.02); *A61B 2050/002* (2016.02); *A61B 2050/0065* (2016.02)

(58) Field of Classification Search
CPC . A61B 50/30; A61B 50/33; A61B 2050/0065; A61B 2050/002; B65D 25/10; B65D 25/108
USPC ...................................................... 206/363
See application file for complete search history.

(56) References Cited

U.S. PATENT DOCUMENTS

| 4,501,363 | A  | * | 2/1985 | Isbey, Jr. ............... | A61B 50/33 |
|---|---|---|---|---|---|
| | | | | | 206/363 |
| 8,118,167 | B2 | | 2/2012 | Togashi et al. | |
| 9,925,327 | B2 | | 3/2018 | Okihara et al. | |
| 11,540,892 | B2 | * | 1/2023 | Yoshida ............... | A61M 5/00 |
| 11,547,518 | B2 | * | 1/2023 | Yoshida ............... | A61B 50/30 |

(Continued)

FOREIGN PATENT DOCUMENTS

DE    103 01 386 A1    11/2003
DE  10 2008 046 378 A1    3/2010

(Continued)

OTHER PUBLICATIONS

Notice of Deficiencies mailed by Israel Patent Office mailed on Dec. 12, 2022, in corresponding Israel patent application No. 288489.

(Continued)

*Primary Examiner* — Steven A. Reynolds
(74) *Attorney, Agent, or Firm* — IP Business Solutions, LLC

(57) ABSTRACT

To provide a packaged medical device in which a medical device in a container is stably fixed and which can be easily opened. Specifically, provided is a packaged medical device comprising a container having an opening portion and a flange portion formed to extend outward in a peripheral portion of the opening portion, a medical device housed inside the container, and a lid member having a gas impermeable film and peelably heat-sealed to the flange portion, in which the inside of the container is set to a negative pressure to the atmospheric pressure so that the medical device is pressed by the lid member and the peel strength to the flange portion of the lid member is 2 to 50 N/in.

7 Claims, 5 Drawing Sheets

(56) References Cited

U.S. PATENT DOCUMENTS

| | | |
|---|---|---|
| 2004/0146669 A1 | 7/2004 | Gollier et al. |
| 2006/0054523 A1 | 3/2006 | Porret et al. |
| 2009/0071960 A1 | 3/2009 | Nagata et al. |
| 2010/0012546 A1* | 1/2010 | Togashi ............... B65D 25/108 |
| | | 206/534.1 |
| 2013/0020328 A1 | 1/2013 | Duan et al. |
| 2014/0087182 A1 | 3/2014 | Matsumoto |
| 2014/0353190 A1 | 12/2014 | Okihara et al. |
| 2015/0209503 A1 | 7/2015 | Amarchinta et al. |
| 2019/0099234 A1 | 4/2019 | Young et al. |
| 2019/0125473 A1 | 5/2019 | Togashi et al. |
| 2021/0068915 A1 | 3/2021 | Togashi et al. |

FOREIGN PATENT DOCUMENTS

| | | |
|---|---|---|
| EP | 3450349 A1 | 3/2019 |
| JP | 1989-164368 A | 6/1989 |
| JP | H01-149724 A | 6/1989 |
| JP | H05-064653 A | 3/1993 |
| JP | 1999-236073 A | 8/1999 |
| JP | 2004-513708 A | 5/2004 |
| JP | 2005-153980 A | 6/2005 |
| JP | 2005-231691 A | 9/2005 |
| JP | 2013-086843 A | 5/2013 |
| JP | 2015-119919 A | 7/2015 |
| JP | 2017-504438 A | 2/2017 |
| JP | 2017-80478 A | 5/2017 |
| JP | 2019-088588 A | 6/2019 |
| WO | 94/19180 A1 | 9/1994 |
| WO | 2008/107961 A1 | 9/2008 |
| WO | 2017/188427 A1 | 11/2017 |

OTHER PUBLICATIONS

International Search Report for corresponding International Patent Application No. PCT/JP2019/028241 dated Aug. 27, 2019.
Notice of Reasons for Refusal mailed by Japanese Patent Office dated Jul. 14, 2020, in corresponding Japanese patent application No. 2019-551402.
Decision of Refusal mailed by Japanese Patent Office dated Feb. 2, 2021, in corresponding Japanese patent application No. 2019-551402.
Notice of Reasons for Refusal mailed by Japanese Patent Office dated Dec. 21, 2021, in corresponding Japanese patent application No. 2019-551402.
Notice of Reasons for Refusal mailed by Japanese Patent Office dated Mar. 22, 2022, in corresponding Japanese patent application No. 2019-551402.
Extended European Search Report mailed by European Patent Office dated May 11, 2022 in corresponding European patent application No. 19937402.6-1113.

* cited by examiner

PACKAGED MEDICAL DEVICE

CROSS-REFERENCE TO RELATED APPLICATIONS

This is a continuation application claiming priority to U.S. patent application Ser. No. 16/493,395, filed on Sep. 12, 2019, which is incorporated herein by reference. The contents of this application are incorporated herein by reference in their entirety.

BACKGROUND OF THE INVENTION

Field of the Invention

The present invention relates to a packaged medical device.

Description of the Related Art

Medical devices are generally sterilized in a state of being housed in a container, and then circulated and stored in the sterilized state. As a method for sterilizing the inside of a container housing products or instruments which are intended to be sterilized, such as medical devices, a technique is known which comprises covering an opening portion in an upper portion of the container with a cover sheet formed of a selectively impermeable material, fixing the cover sheet for sealing, and then sterilizing the inside of the container by irradiation with electron beams (Patent Document 1).

However, according to the technique described in Patent Document 1, there is a possibility that the medical devices vibrate in the container in conveyance, so that the medical devices are damaged or fine particles are generated due to friction to cause a sanitary problem.

In order to solve the above-described problems, a method for fixing medical devices in a container to suppress the vibration of the medical devices in conveyance has been proposed. For example, a method is known which comprises placing a container holding a plurality of syringe barrels in a bag containing a gas impermeable film, and then bringing the inside of the bag into a decompressed state (Patent Document 2). According to this method, the gas impermeable film is brought into a close contact with flange portions of the syringe barrels held in the container, and therefore the syringe barrels are fixed, so that the vibration during conveyance is reduced.

CITATION LIST

Patent Documents

[Patent Document 1] JP-T No. 2004-513708
[Patent Document 2] WO No. 2008/107961

SUMMARY OF THE INVENTION

A bag packaging contents by bringing the inside into a decompressed state is generally referred to as a vacuum bag. According to the method described in Patent Document 2 in which contents are fixed using the vacuum bag, it is difficult to adjust the pressure in the vacuum bag, so that the fixed states of the medical devices vary in some cases. Moreover, when a worker performs work of disposing a container housing medical devices in the vacuum bag, and then decompressing the inside thereof, it is difficult to equalize the air quantity remaining inside the vacuum bag and the position of the container in the vacuum bag for each worker and each product and the decompressed state becomes uneven, so that the fixed states of the medical devices vary in some cases. Thus, there is a possibility that the fixation of the medical devices by the vacuum bag lacks stability.

Thus, the present inventors have extensively examined a packaged medical device in which medical devices in a container can be stably fixed. As a result, the present inventors have newly found a configuration in which a lid member having a gas impermeable film is heat-sealed to an opening portion of a container, the inside of the container is set to a negative pressure to the atmospheric pressure to thereby bend the lid member toward the inside of the container, and a medical device is fixed by the bent portion.

The present inventors have further examined the packaged medical device provided with the above-described configuration. As a result, the fixed state of the medical devices is further stabilized by firmly heat-sealing the lid member but strong external force is required for peeling the lid member, so that there is a possibility that contents jump out in opening. Therefore, the present inventors have focused on the fact that easy openability is also an important element.

In view of the above-described circumstances, it is a primary object of the present invention to provide a packaged medical device in which a medical device in a container is stably fixed and which can be easily opened.

Solution to Problem

More specifically, the present invention provides a packaged medical device comprising a container having an opening portion and a flange portion formed to extend outward in a peripheral portion of the opening portion, a medical device housed inside the container, and a lid member having a gas impermeable film and peelably heat-sealed to the flange portion, in which the inside of the container is set to a negative pressure to the atmospheric pressure so that the medical device is pressed by the lid member and the peel strength to the flange portion of the lid member is 2 to 50 N/in.

The pressure inside the container may be 400 to 1013 hPa.

The lid member may be peelably heat-sealed to the flange portion through an adhesive or an adhesive layer configuring the lid member.

The adhesive or the adhesive layer configuring the lid member may comprise an olefin-based resin.

The lid member may be peelable from the flange portion by interfacial peeling or cohesive peeling.

The lid member may comprise the gas impermeable film and a gas permeable film provided on the side of the container of the gas impermeable film.

In the present invention, "the medical device is pressed by the lid member" means that the medical device is directly or indirectly pressed by the lid member. More specifically, the present invention includes a case where the lid member is in contact with the medical device and directly presses the medical device and a case where the lid member is in contact with a substance other than the medical device (for example, a holder holding the medical device) and indirectly presses the medical device by pressing the substance other than the medical device.

Advantageous Effects of Invention

The present invention can provide a packaged medical device in which a medical device in a container is stably fixed and which can be easily opened. The effects of the present invention are not necessarily limited to the effects described herein and may be any effect described in this specification.

DETAILED DESCRIPTION

Figure 1:
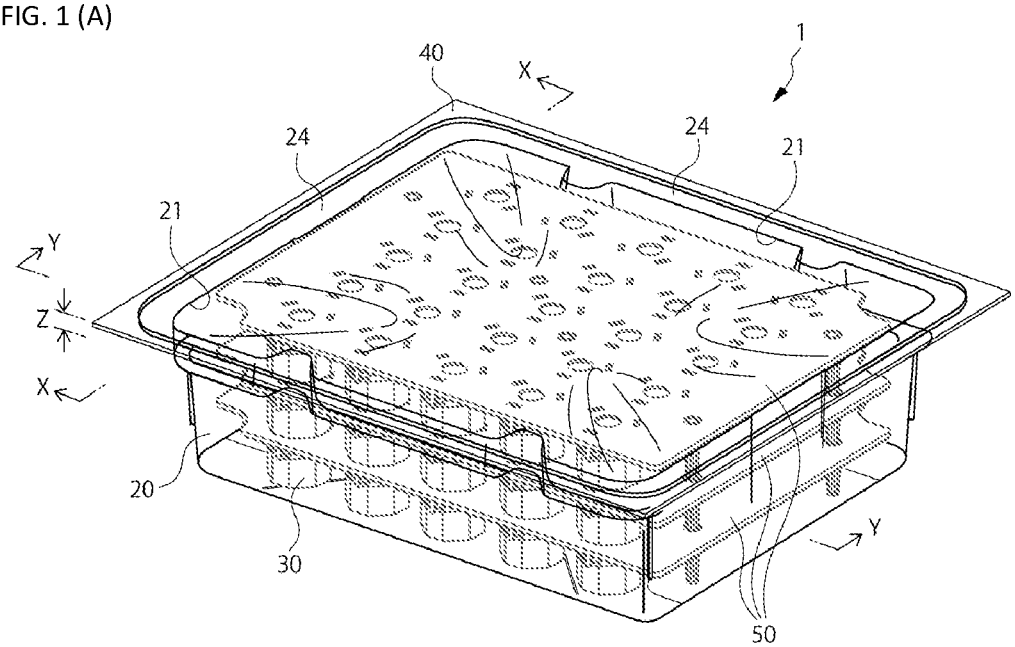
FIG. 1A is a perspective view illustrating a packaged medical device 1.
FIG. 1B is a cross-sectional view in an arrow Y direction of the packaged medical device 1 cut along the X-X line, the Y-Y line, and the Z-Z line of FIG. 1A.
Figure 1:
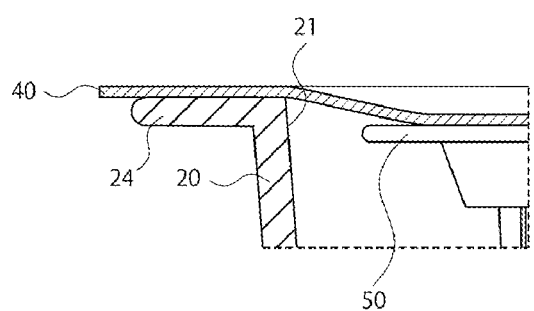

Hereinafter, embodiments of the present invention are described with reference to the drawings. The embodiments described below give typical embodiments of the present invention and the scope of the present invention is not narrowly interpreted by the embodiments.

<1. Packaged Medical Device>

(1) Entire Configuration

First, the entire configuration of a packaged medical device according to one embodiment of the present invention is described with reference to FIG. 1. FIG. 1A is a perspective view illustrating a packaged medical device 1. FIG. 1B is a cross-sectional view in an arrow Y direction of the packaged medical device 1 cut along the X-X line, the Y-Y line, and the Z-Z line of FIG. 1A. The packaged medical device 1 is provided with a container 20 having an opening portion 21 and a flange portion 24 formed to extend outward in a peripheral portion of the opening portion 21 as illustrated in FIG. 1A. The packaged medical device 1 is further provided with medical devices 30 housed inside the container 20 and a lid member 40 sealing the opening portion 21 of the container 20 by being peelably heat-sealed to the flange portion 24.

It is preferable that the container 20 is provided with holding portions 50 holding the medical devices 30 as illustrated in FIG. 1A. By providing the holding portions 50, the medical devices 30 can be more stably fixed, so that the rattling of the medical devices 30 in the container 20 can be effectively suppressed. In the example illustrated in FIG. 1A, the holding portions 50 holding the medical devices 30 are vertically stacked in three stages. However, the number of the holding portions 50 is not limited thereto and may be one or two or more.

The inside of the container 20 is set to a negative pressure to the atmospheric pressure. Therefore, the lid member 40 covering the opening portion 21 of the container 20 is bent toward the inside of the container 20 as illustrated in FIG. 1B. The holding portion 50 is pressed by the bent portion of the lid member 40. In this specification, the atmospheric pressure is the standard pressure and is specifically 1013.25 hPa.

When the manufactured packaged medical device is placed in an environment lower than the atmospheric pressure by air transport or the like, the pressure in the container may be set to be equal to or less than the pressure under the air transport. The upper limit of the pressure inside the container 20 is preferably 1013 hPa and more preferably 980 hPa. The lower limit of the pressure may be adjusted as appropriate according to the material, the size, and the like of the container so that the container 20 is not deformed or damaged and is preferably 400 hPa or more.

The medical devices 30 illustrated in FIG. 1A are pressed by the lid member 40 through the holding portions 50. Thus, the holding portions 50 and the medical devices 30 are held and fixed between a bottom surface portion of the container 20 and the lid member 40, and therefore the holding portions 50 and the medical devices 30 are hard to vibrate during conveyance of the packaged medical device 1. Moreover, the exterior of the packaged medical device 1 can be sterilized by being packaged with the lid member 40. A method for sterilizing the exterior is not particularly limited and an arbitrary method by which the sterilization effect is obtained may be selected.

The packaged medical device 1 of this embodiment can fix the medical devices 30 by the lid member 40 covering the opening portion 21 of the container 20 without using the vacuum bag covering the entire container described in Patent Document 2. Therefore, a variation in the fixed states of the medical devices which may occur when the vacuum bag is used is hard to occur. Moreover, there are also advantages, such as a cost reduction of packaging materials and a reduction in process in opening the packaging material.

In general, when medical devices are conveyed in a non-fixed state, the medical devices move or vibrate to rub against each other in a container, so that there is a possibility that the surface is damaged or fine particles are generated. Meanwhile, the packaged medical device 1 of this embodiment can fix the medical devices 30 in the container 20, and therefore can suppress the generation of damages or fine particles.

Packaged medical devices are generally sterilized by irradiation with radiation in many cases. Oxygen present in containers housing medical devices may be activated by irradiation with radiation to generate ozone gas. When contents, such as medical devices, and containers are formed of a synthetic resin, the synthetic resin deteriorates by the ozone gas in some cases. The main chain and the side chain of the synthetic resin are cut by the irradiation with radiation and react with oxygen to thereby generate volatile substances in some cases. The volatile substances may cause an irradiated odor after the irradiation with radiation. Meanwhile, the packaged medical device 1 of this embodiment can reduce the oxygen amount inside the container 20 by setting the inside of the container 20 to a negative pressure to the atmospheric pressure. Therefore, the generated ozone gas decreases, so that the degradation of the synthetic resin is suppressed and the irradiated odor after the irradiation with radiation is reduced. In order to further reduce the oxygen amount in the container 20, the air remaining in the container 20 may be replaced by an inert gas, such as nitrogen.

(2) Container 20

Figure 2:
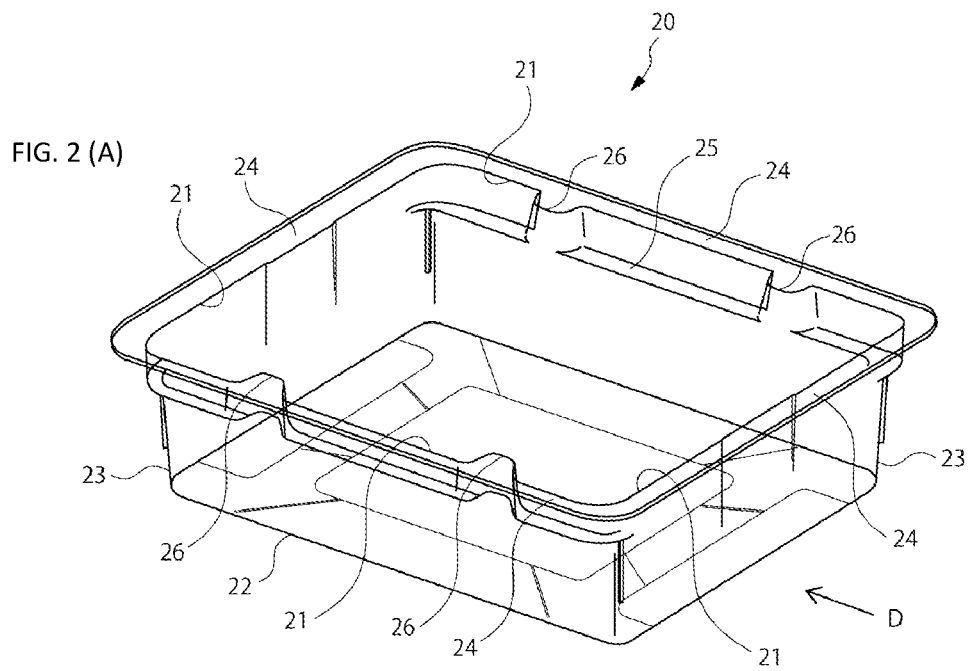
FIG. 2A is a perspective view illustrating a container 20.
FIG. 2B is a front view illustrating the container 20 viewed from an arrow D direction in FIG. 2A.
Figure 2:
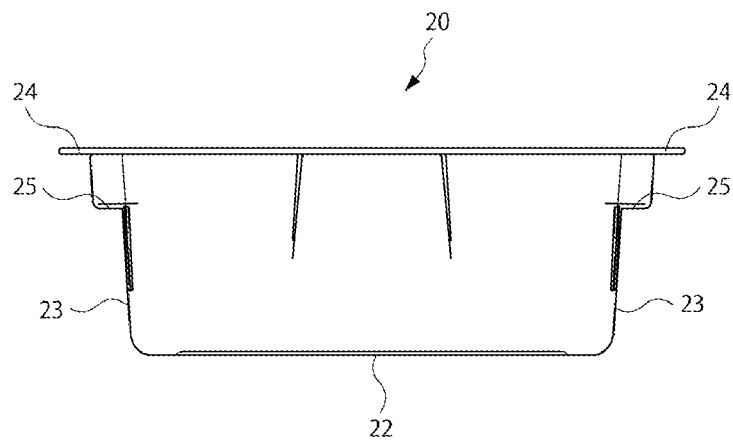

Next, the container 20 is described with reference to FIGS. 2. FIG. 2A is a perspective view illustrating the container 20. FIG. 2B is a front view illustrating the container 20 viewed from an arrow D direction in FIG. 2A. The shape of the container 20 is not particularly limited insofar as the opening portion 21 is provided. For example, the container 20 can be formed into a box shape provided with a bottom surface portion 22 of a substantially rectangular shape, a side peripheral portion 23 extending upward from the periphery of the bottom surface portion 22, and the opening portion 21 surrounded by the upper end of the side peripheral portion 23 as illustrated in FIGS. 2A and 2B. The shape of the bottom surface portion 22 may be an arbitrary shape, such as a polygonal shape, a circular shape, and an oval shape, other than the substantially rectangular shape.

As illustrated in FIGS. 2A and 2B, the container 20 has a flange portion 24 formed to extend outward in a peripheral portion of the opening portion 21. The lid member is heat-sealed to the flange portion 24, whereby the opening portion 21 is sealed.

Moreover, the container 20 can be provided with level difference portions 25, which are provided to horizontally project inward at positions apart by a predetermined length from the flange portion 24 positioned in the upper end toward the bottom surface portion 22 (downward direction), in the longitudinal direction of the container 20 as illustrated in FIGS. 2A and 2B. The level difference portion 25 can also be provided on the entire periphery of the container 20 (side peripheral portion 23). By providing the level difference portions 25, when a person or a machine grasps the outside of the packaged medical device 1 (see FIG. 1A), a finger or an arm of the machine can be hooked on the level difference portions 25, and therefore the packaged medical device 1 can be stably grasped.

The container 20 can be further provided with projection portions 26 projecting inward on the side peripheral portion 23 as illustrated in FIG. 2A. When a gap is present between the holding portions 50 (see FIG. 1A) and the side peripheral portion 23, the vibration of the holding portions 50 in the container 20 can be suppressed by filling the gap with the projection portions 26. In the example illustrated in FIG. 2A, the projection portions 26 are provided on the side peripheral portion 23 between the flange portion 24 and the level difference portions 25. The number of the projection portions 26 is two in each of a pair of facing surfaces of the side peripheral portion 23, i.e., four in total. However, the position and the number of the projection portions 26 are not limited thereto and may be adjusted as appropriate so as to fill the gap between the container 20 and the holding portions 50.

Materials of the container 20 are preferably selected from the viewpoints that the materials are non-toxic and sanitary, various sterilization methods are applicable to the materials, the materials have lightfastness and weatherability, and the like. Furthermore, the materials of the container 20 are preferably selected also considering the oxygen permeability in order to maintain the inside of the container 20 in a negative pressure relative to the atmospheric pressure. The oxygen permeability of the container 20 is described later. The materials of the container 20 are not particularly limited and may be polypropylene (PP), polycarbonate (PC), polyethylene (PE), high impact polystyrene (HIPS), and the like, for example. FIGS. 1 and FIGS. 2 illustrate a case where the container 20 is formed of a transparent material. However, the materials of the container 20 may not be transparent and are not particularly limited in transparency.

Medical Device 30

Next, the medical devices 30 housed in the container 20 are described with reference to FIG. 1A again. FIG. 1A illustrates caps put on rubber plugs sealing mouth portions of pharmaceutical agent containers or the like for preventing the removal of the rubber plugs as an example of the medical devices 30. The medical device 30 is not limited to the cap and widely includes substances which are instruments to be used in a medical field and which may be housed in containers, such as pharmaceutical agent containers, rubber plugs for pharmaceutical agent containers, syringes, pistons, injection needles, and vials, for example.

(4) Lid Member 40

The lid member 40 has a gas impermeable film and is peelably heat-sealed to the flange portion 24 of the container 20 to thereby seal the opening portion 21 as illustrated in FIG. 1A. The lid member 40 is a sheet-like member and is not a member of a bag shape, such as a vacuum bag. Although FIGS. 1 illustrate the case where the lid member 40 is formed of a transparent material, the materials of the lid member 40 may not be transparent and are not particularly limited in transparency.

The peel strength to the flange portion 24 of the lid member 40 is 2 to 50 N/in. When the peel strength is less than 2 N/in., there is a possibility that the lid member 40 is peeled by the vibration of the container 20. When the peel strength exceeds 50 N/in., the opening of the packaged medical device 1 is difficult, or, even when the packaged medical device 1 can be opened, contents jump out in some cases.

The peel strength is a value measured by inserting a test piece 1 in. in width and 4 in. in length produced from the lid member 40 into a chuck of a load cell mounted in a tensile tester (Autograph AG-5kNIS, manufactured by Shimadzu Corporation) and performing a 90° peel test under the condition of tensile speed of 300 mm/min.

The peeling form of the lid member 40 is preferably interfacial peeling or cohesive peeling. From the viewpoint of preventing the mixing of fine particles, such as seal pieces, into the container 20 when peeling the lid member, the interfacial peeling is preferably adopted. From the viewpoint of reducing a variation in the peel strength for each product, the cohesive peeling is preferably adopted.

The heat-sealing of the lid member 40 and the flange portion 24 may be performed by known methods. For example, a method for melting the flange portion 24 with heat to fuse the flange portion 24 to the lid member 40, a method for melting an adhesive layer configuring the lid member 40 with heat to fuse the lid member 40 to the flange portion 24, a method for fusing the lid member 40 and the flange portion 24 with each other through an adhesive (for example, a hot melt), and the like are mentioned. Among the above, the lid member 40 and the flange portion 24 are preferably heat-sealed to each other through the adhesive or the adhesive layer configuring the lid member 40. The adhesive or the adhesive layer configuring the lid member 40 preferably comprises an olefin-based resin and is more preferably an easy peel agent. The adhesive layer configuring the lid member 40 is described in detail later.

The configuration of the lid member 40 is not particularly limited insofar as a gas impermeable film is provided and preferably comprises a laminate containing a (A) gas impermeable layer, a (B) anchor coat layer, and a (C) adhesive layer in order from the upper layer (outside). Hereinafter, each layer is described.

(A) Gas Impermeable Layer

The gas impermeable layer is a layer having a gas impermeable film. The gas impermeable layer is preferably one containing only a gas impermeable film (A-1) or one containing a gas impermeable film and other layers (A-2).

(A-1) Case of Gas Impermeable Layer Containing Only Gas Impermeable Film

First, a case where the gas impermeable layer is formed of only a gas impermeable film is described.

The gas impermeable film is a film having a gas barrier property which is completely impermeable to gas or has an excessively low gas permeation amount. Examples of the type of the gas impermeable film include, for example, metal films containing aluminum, silver, gold, and the like, metal vapor-deposited films in which aluminum, silver, gold, and the like are vapor-deposited on the surface, inorganic substance vapor-deposited films in which SiOX and the like are vapor-deposited on the surface, gas barrier resin films, and the like.

Raw materials forming the gas barrier resin film are preferably polyester, such as polyethylene terephthalate (PET), polypropylene (PP), polyethylene (PE), polyvinyl alcohol, an ethylene-vinyl alcohol copolymer, polyvinyl chloride, polyvinylidene chloride, polyvinylidene chloride-polyvinyl chloride, a polyvinylidene chloride-acrylic acid ester copolymer, biaxially oriented polypropylene (OPP), nylon, and biaxially oriented nylon.

The gas impermeable film may have a monolayer structure or a multilayer structure. As the gas impermeable film of a monolayer structure, a monolayer gas barrier resin film is preferably used. As the gas impermeable film of a multilayer structure, a multilayer film in which a plurality of gas barrier resin films is laminated, a multilayer film in which a plurality of metal films is laminated, a multilayer film in which a gas barrier resin film and a metal film are laminated, and the like are usable, for example.

(A-2) Case of Gas Impermeable Layer Containing Gas Impermeable Film and Other Layers Next, a case where the gas impermeable layer is formed of a gas impermeable film and other layers is described. Examples of the other layers include, for example, a moisture absorbing layer, a moisture-proof layer, a light shielding layer, and a printing layer.

The gas impermeable layer may have a moisture absorbing layer or a moisture-proof layer on the lower surface side (container 20 side) of the gas impermeable film. Thus, the dry state in the container 20 can be maintained for a longer period of time.

The gas impermeable layer may be provided with a light shielding layer irrespective of the upper surface side (outside) or the lower surface side (container 20 side) of the gas impermeable film. Thus, the photodegradation of the medical device 30 can be effectively prevented. The light shielding layer can be configured to have low UV transmittance or configured to have high UV absorptivity irrespective of colored or colorless by known methods.

The gas impermeable layer may be provided with a printing layer for indicating necessary items, such as the name and the size of a medical device to be housed and, when the medical device is a prefilled syringe, for example, the name of a pharmaceutical agent to be filled into the syringe and the filling amount thereof on the upper surface side (outside) of the gas impermeable film.

(B) Anchor Coat Layer

The anchor coat layer is provided on the lower surface side (container 20 side) of the (A) gas impermeable layer. The anchor coat layer is located between the (A) gas impermeable layer and the (C) adhesive layer described above and is provided in order to improve the adhesiveness between the gas impermeable layer and the adhesive layer. Although raw materials forming the anchor coat layer may be selected according to materials of the gas impermeable layer and the adhesive layer and are preferably polyethylene and biaxially oriented nylon. The anchor coat layer may have a monolayer structure or may have a multilayer structure. The anchor coat layer is more preferably a monolayer film containing a polyethylene film or a multilayer film in which Polyethylene film/Biaxially oriented nylon film/Polyethylene film/are laminated in order.

(C) Adhesive Layer

The adhesive layer is provided at least in a portion corresponding to the flange portion 24 of the container 20 on the lower surface side (container 20 side) of the (B) anchor coat layer. The adhesive layer is preferably an easy peel layer in order to peelably heat-seal the lid member 40 to the flange portion 24 and can be formed by the following known easy peel agents. When the flange portion 24 is formed of polypropylene, an ethylene-vinyl acetate resin, an ethylene-acrylic acid resin, an olefin-based resin containing a mixture of polypropylene and polyethylene or the like, a two-component curable urethane-based dry laminate adhesive, and the like are usable as raw materials forming the adhesive layer. When the flange portion 24 is formed of polyvinyl chloride, olefin-based resins, such as an ethylene-vinyl acetate resin and an ethylene-acrylic acid resin, those in which a styrene-butadiene block copolymer is blended with polystyrene, a vinyl chloride-vinyl acetate copolymer, a two-component curable urethane-based dry laminate adhesive, and the like are usable as raw materials forming the adhesive layer. When the flange portion 24 is formed of polyester, olefin-based resins, such as an ethylene-vinyl acetate resin and an ethylene-acrylic acid resin, copolyester, a two-component curable urethane-based dry laminate adhesive, and the like are usable as raw materials forming the adhesive layer. Among the above, the adhesive layer is preferably formed of an easy peel agent containing the olefin-based resin. The adhesive layer may be formed only at a position corresponding to the flange portion 24 on the lower surface side (container 20 side) of the anchor coat layer from the viewpoint of preventing the adhesion of the adhesive to contents.

When "(A) Gas impermeable layer/(B) Anchor coat layer/(C) Adhesive layer" in order from the upper layer is indicated as a preferable configuration of the lid member 40, preferable raw materials of each layer are described in the following (1) to (4). (1) to (3) indicate the lid member 40 having a three-layer structure and (4) indicates the lid member 40 having a five-layer structure:

(1) (A) Polyethylene terephthalate/(B) Polyethylene/(C) Polyethylene-based resin,
(2) (A) Polyethylene terephthalate/(B) Polyethylene/(C) Olefin-based resin containing a mixture of polyethylene and polyethylene terephthalate,
(3) (A) Polyethylene terephthalate/(B) Polyethylene/(C) Polypropylene-based resin, and
(4) (A) Polyethylene terephthalate/(B) Polyethylene/(B) Biaxially oriented nylon/(B) polyethylene/(C) Polyethylene-based resin.

When the lid member 40 is provided with a laminate containing the (A) gas impermeable layer, the (B) anchor coat layer, and the (C) adhesive layer, the gas permeable film may be placed on the medical devices 30 or the holding portions 50 inside the container 20, and then the laminate may be heat-sealed to the flange portion 24. This can prevent the contamination of the inside of the container 20 in peeling the lid member 40. Moreover, after the gas permeable film is placed, the inside of the container 20 is sterilized before heat-sealing the laminate, whereby the degree of sanitation of the inside of the container 20 can be further increased.

The lid member 40 may be provided with a (D) gas permeable film in addition to the (A) gas impermeable layer, the (B) anchor coat layer, and the (C) adhesive layer described above. Hereinafter, a case where the lid member 40 is provided with the (D) gas permeable film is described.

(D) Gas Permeable Film

The gas permeable film is preferably a sterilizable film. The sterilizable film allows the permeation of gases for sterilization, such as gas and vapor, but does not allow the permeation of bacteria and contains filaments of high-density polyethylene or other polymers, for example. Examples of commercially-available items of the sterilizable gas permeable film include Tyvek (Registered Trademark) manufactured by Du Pont and the like, for example.

In the lid member 40, the gas permeable film is preferably positioned on the lower surface side (container 20 side) relative to the gas impermeable film. When the lid member 40 is provided with the laminate containing the (A) gas impermeable layer, the (B) anchor coat layer, and the (C) adhesive layer, the gas permeable film is preferably provided on the lower surface side (container 20 side) of the (C) adhesive layer. Thus, the gas permeable film is preferably disposed on the bottom layer of the lid member 40 to configure the lowest surface of the lid member 40. In this case, the gas permeable film is peelably heat-sealed to the flange portion 24 of the container 20. The peel strength to the flange portion of the lid member 40 provided with the gas permeable film is 2 to 50 N/in as described above.

Although a method for heat-sealing the gas permeable film to the flange portion 24 is not particularly limited, a method for heat-sealing the gas permeable film to the flange portion 24 through an adhesive is preferably used. The adhesive may be an easy peel agent similar to the (C) adhesive layer. The adhesive may be provided at least between the gas permeable film and the flange portion 24.

In forming the lid member 40, it is preferable that the (D) gas permeable film is first peelably heat-sealed to the flange portion 24, and then the gas impermeable film or the laminate containing the (A) gas impermeable layer, the (B) anchor coat layer, and the (C) adhesive layer is laminated and bonded. Thus, the gas permeable film is heat-sealed, and then the inside of the container 20 can be sterilized before the gas impermeable film or the laminate is bonded, whereby the degree of sanitation of the inside of the container 20 can be further increased. A bonding method is not particularly limited and known methods, such as a method of bonding the gas impermeable film or the laminate through the (C) adhesive layer and a method for bonding the gas impermeable film or the laminate through an adhesive, can be adopted. The gas impermeable film or the laminate may be peelable or may be unpeelable with respect to the gas permeable film. In order to prevent the contamination of the inside of the container 20 in peeling the lid member 40, a gas permeable film may be further placed on the medical devices 30 or the holding portions 50 inside the container 20 separately from the (D) gas impermeable film configuring the lid member 40.

The lid member 40 has a gas barrier property by having the gas impermeable film. As the index indicating the gas barrier property of the lid member 40, the oxygen permeability is mentioned. In the lid member 40, the oxygen permeability at 23±2° C. is preferably 0 to 100 cm$^3$/m$^2$·19 24 h·atm and more preferably 0 to 50 cm$^3$/m$^2$·24 h·atm. Thus, the state where the inside of the container 20 of the packaged medical device 1 is set to the negative pressure to the atmospheric pressure can be maintained for a longer period of time. In this specification, the oxygen permeability of the gas impermeable film is a value measured based on Japanese Industrial Standards JIS K 7126. The oxygen permeability is a value of the entire lid member 40 and, when layers other than the gas impermeable film are present, is a value also including the oxygen permeability of the other layers.

In the packaged medical device 1 of this embodiment, it is preferable that the container 20 has high gas barrier property equal to that of the lid member 40 in order to maintain the negative pressure state in the container 20, i.e., the value of the oxygen permeability of the container 20 is preferably close to the value of the lid member 40. Specifically, an absolute value of a difference between the oxygen permeability of the lid member 40 and the oxygen permeability of the container 20 at 23±2° C. is preferably 200 cm$^3$/m$^2$·24 h·atm or less.

The thickness of the lid member 40 may be selected as appropriate according to configurations or materials. For example, when the lid member 40 contains the laminate containing the (A) gas impermeable layer, the (B) anchor coat layer, and the (C) adhesive layer, the thickness of the lid member 40 is preferably 50 to 150 μm and more preferably 70 to 100 μm. The lid member 40 contains the laminate of the (A) gas impermeable layer, the (B) anchor coat layer, and the (C) adhesive layer and the (D) gas permeable film, the thickness of the lid member 40 is preferably 200 to 500 μm.

(5) Holding Portion 50

Figure 3:
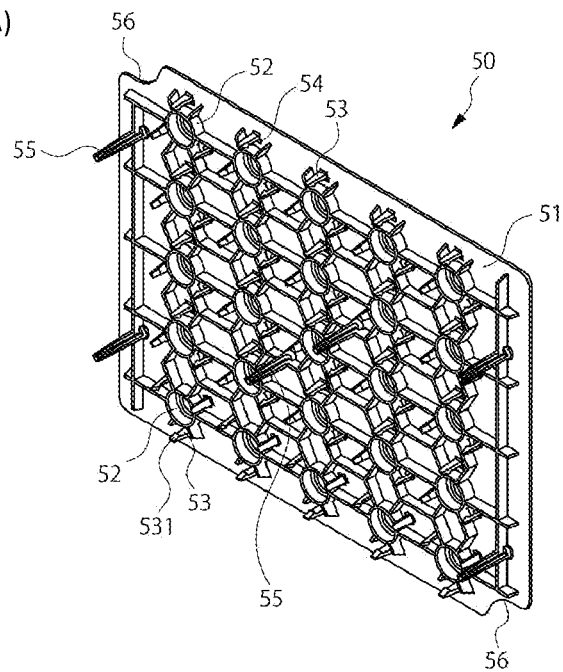
FIG. 3A is a perspective view illustrating a holding portion 50.
FIG. 3B is a plan view illustrating the holding portion 50.
FIG. 3C is a front view illustrating the holding portion 50.
Figure 3:
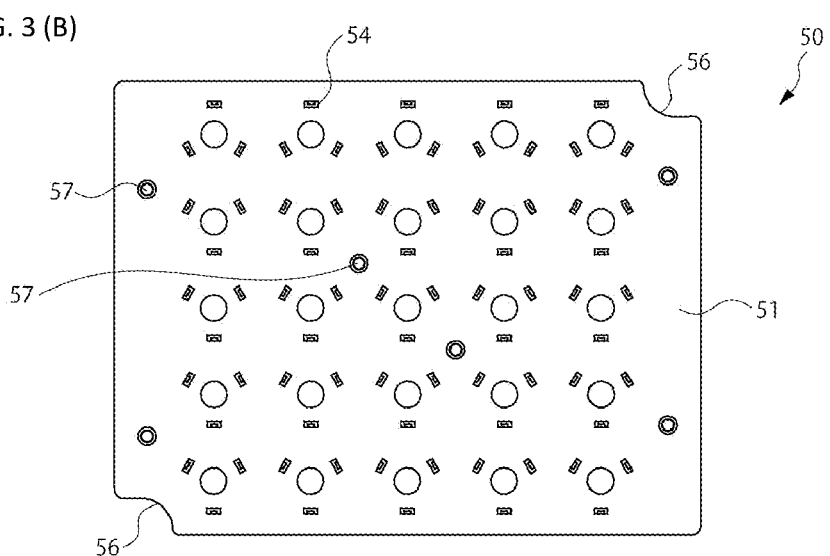
Figure 3:
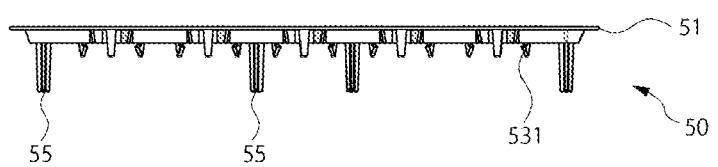

It is preferable that the packaged medical device 1 according to this embodiment is provided with the holding portions 50 holding the medical devices 30 inside the container 20 as illustrated in FIG. 1A. Although the shape of the holding portion 50 may be designed as appropriate according to the type, the size, and the like of the medical devices 30 and is not particularly limited, an example thereof is described with reference to FIGS. 3 and 4. FIG. 3A is a perspective view illustrating the holding portion 50. FIG. 3B is a plan view illustrating the holding portion 50. FIG. 3C is a front view illustrating the holding portion 50.

The holding portion 50 is provided with a plate-like substrate portion 51 as illustrated in FIGS. 3A to 3C. The shape of the substrate portion 51 may be an arbitrary shape, such as a polygonal shape, a circular shape, and an oval shape, other than the substantially rectangular shape illustrated in the figures and is preferably selected according to the shape of a container where the holding portion 50 is housed.

The holding portion 50 is provided with a plurality of cylindrical portions 52 projecting from the substrate portion 51 as illustrated in FIG. 3A. The installation number of the cylindrical portions 52 and the interval with the adjacent cylindrical portions 52 is not particularly limited and may be set as appropriate according to the size and the like of medical devices to be held.

As illustrated in FIGS. 3A and 3C, the substrate portion 51 can be provided with a locking projection portion 53 projecting from the substrate portion 51 and having a locking claw 531 in a tip portion around the cylindrical portion 52. When the substrate portion 51 is turned upward, the locking claw 531 projects downward relative to the cylindrical portion 52. In the example illustrated in FIG. 3A, three locking projection portions 53 are disposed around each of the cylindrical portions 52 but the arrangement number is not limited thereto.

The holding portion 50 can stably hold a medical device (not illustrated) by housing the medical device inside the cylindrical portion 52 and locking the medical device with the locking projection portions 53.

The substrate portion 51 can be provided with through-holes 54 as illustrated in FIGS. 3A and 3B. By providing the through-holes 54, a sterilizing fluid sufficiently spreads in the container, so that the sterilization efficiency is improved. The shape of the through-hole 54 is not particularly limited and may be an arbitrary shape, such as a rectangular shape, a polygonal shape, a circular shape, and an oval shape. In the example illustrated in FIGS. 3A and 3B, three through-holes 54 are disposed around each of the cylindrical portions 52 but the arrangement position and number are not limited thereto.

The substrate portion 51 can be provided with notch portions 56 having such a size that a finger can be inserted thereinto as illustrated in FIGS. A and B. Thus, work of housing the holding portion 50 in the container or taking out the holding portion 50 from the container can be more easily performed. The notch portions 56 can be provided for the purpose of, when a plurality of machines shares work of stacking the holding portion 50 holding caps on the holding portion 50 holding vials and work of moving the stacked holding portions 50, for example, preventing interference of each machine. The position of the holding portion 50 can be accurately grasped by detecting the notch portions 56 with an image inspection machine or the like. Therefore, abnormalities in conveyance and positional shift of the holding portions 50 can be detected in an early stage and facility stop time accompanying the abnormalities in conveyance or positional shift can be reduced. In the example illustrated in FIGS. 3A and 3B, the notch portions 56 are provided in two places on the diagonal line among the four corners of the substrate portion 51 but the position and the number are not particularly limited thereto.

The substrate portion 51 can be provided with support portions 55 projecting from the substrate portion 51 as illustrated in FIGS. 3A and 3C. When the substrate portion 51 is turned upward, the support portions 55 project downward relative to the cylindrical portions 52 and the locking projection portions 53. As described later, when the holding portion 50 are stacked in multiple stages, the contact of the vertically adjacent holding portions 50 can be prevented and a gap is formed between the vertically adjacent holding portions 50 by providing the support portions 55, and therefore a sterilizing fluid sufficiently spreads, so that the sterilization efficiency is improved. Furthermore, by providing the support portions 55, crushing of the medical devices 30 can be prevented and the medical devices held by the holding portions 50 can be prevented from contacting the bottom surface of the container or moisture and the like accumulated in the bottom surface, so that the sanitary conditions of the medical devices is maintained.

Figure 4:
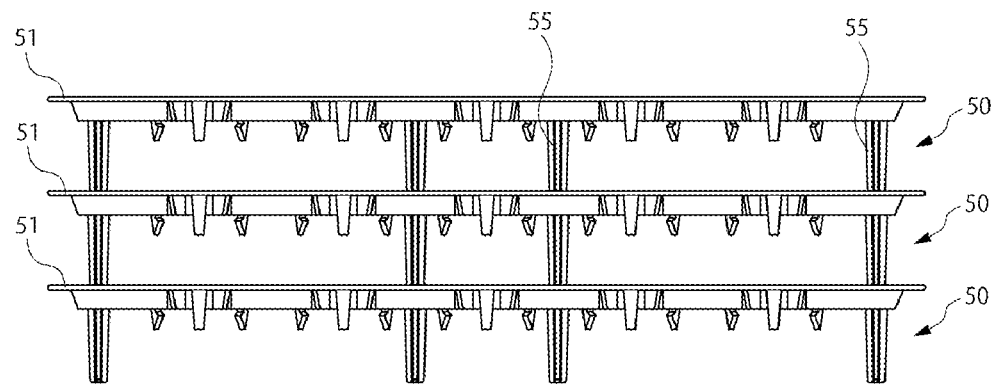
FIG. 4 is a front view illustrating a state where the holding portions 50 are stacked in multiple stages.

FIG. 4 is a front view illustrating a state where the holding portions 50 are stacked in multiple stages. The holding portions 50 can be stacked in multiple stages as illustrated in FIG. 4. In this case, it is preferable that the substrate portion 51 has connection holes 57 as illustrated in FIG. 3B. By fitting the tips of the support portions 55 into the connection holes 57 of the already placed holding portion 50, the holding portions 50 can be stably stacked in multiple stages. The shapes of the support portion 55 and the connection hole 57 are not particularly limited and an arbitrary shape can be adopted.

Materials of the holding portion 50 are preferably selected from the viewpoints of the shape, material, demanded quality, function, strength, and the like of the medical devices 30 in addition to the viewpoints that the materials are non-toxic and sanitary, various sterilization methods are applicable to the materials, the materials have lightfastness and weatherability, and the like. The materials of the holding portion 50 are not particularly limited and may be polyethylene, polycarbonate, polypropylene, polyacetal, and the like, for example.

<2. Method for Manufacturing Packaged Medical Device>

Figure 5:
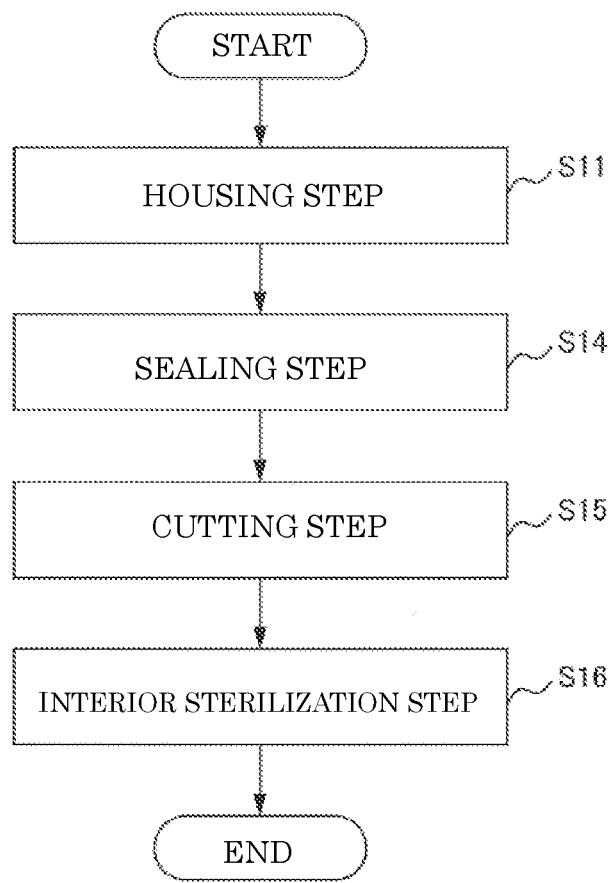
FIG. 5 is a flow chart illustrating an example of a method for manufacturing a packaged medical device.

Next, a method for manufacturing a packaged medical device according to one embodiment of the present invention is described with reference to FIG. 5. FIG. 5 is a flow chart illustrating an example of the method for manufacturing a packaged medical device. The manufacturing method of this embodiment comprises a housing step (Step S11) of housing medical devices inside a container having an opening portion and a flange portion and a sealing step (Step S14) of peelably heat-sealing the lid member to the flange portion to thereby seal the opening portion and setting the inside of the container to a negative pressure to the atmospheric pressure to thereby bring the medical devices into a state of being pressed by the lid member. Thus, the packaged medical device described above may be manufactured.

The medical devices may be those held by a holding portion. In this case, in the housing step (Step S11), the holding portion holding the medical devices is housed inside the container.

In the sealing step (Step S14), the pressure inside the container is decompressed to bring the inside of the container into a negative pressure state to the atmospheric pressure so that the lid member presses the medical devices. The decompression conditions may be adjusted as appropriate according to the material, the size, and the like of the container so that the container is not deformed or broken by the decompression. When the manufactured packaged medical device is placed in an environment lower than the atmospheric pressure by air transport or the like, the pressure in the container can be set to be equal to or less than the pressure under the air transport.

The lid member is heat-sealed to the container in a state of contacting the medical device or a holder to directly or indirectly press the medical device by passing through the sealing step (Step S14). Thus, the packaged medical device in a state where the medical devices are fixed is obtained. A heat-sealing method is not particularly limited and known methods, such as a method for melting the flange portion with heat to fuse the flange portion to the lid member, a method for melting the adhesive layer of the lid member with heat to fuse the lid member to the flange portion, and a method for fusing the lid member and the flange portion with each other by constituent components (for example, adhesives, such as a hot melt) other than the lid member and the flange portion, can be adopted.

In the sealing step (Step S14), specific treatment methods are not particularly limited insofar as the sealing of the opening portion of the container and the pressing of the medical devices by the lid member are achieved as described above. An example of the treatment in the sealing step includes a method for heat-sealing the lid member to the flange portion in the state where the pressure inside the container is a negative pressure to the atmospheric pressure to seal the opening portion in the state where the medical devices are pressed by the lid member. Another example includes a method for heat-sealing the lid member to the flange portion in the normal pressure environment, sucking air from a hole formed beforehand in a side peripheral portion or a bottom surface portion of the container to bring the inside of the container into a negative pressure state to the atmospheric pressure, and then sealing the hole using a lid, a seal, or the like.

In the sealing step (Step S14), the air inside the container may be replaced by inert gas, such as nitrogen. Thus, the oxygen amount inside the container is further reduced, so that the degradation of the synthetic resin configuring the container and the like and the irradiated odor after radiation sterilization can be more effectively suppressed.

The manufacturing method of this embodiment preferably comprises a cutting step (Step S15) of cutting the lid member in or after the sealing step (Step S14). The "in or after the sealing step" means simultaneously with the sealing step or after the sealing step. More specifically, in the manufacturing method of this embodiment, the lid member is preferably cut simultaneously with the heat-sealing of the lid member to the flange portion of the container or after the heat-sealing. For example, when a packaged medical device is manufactured using a lid member larger than the outer shape of the container, such as a roll-shaped lid member, a step of cutting the lid member according to the shape of the container is performed in some cases. By performing the cutting of the lid member in and after the sealing step, the lid member can be more surely heat-sealed.

In the manufacturing method of this embodiment, the sealing step (Step S14) can also be performed in or after the cutting step (Step S15). For example, when the cut lid member is disposed in a decompressed environment together with the container and the like, and then the lid member and the flange portion are heat-sealed to each other, the sealing step may be performed after the cutting step.

In the manufacturing method of this embodiment, an interior sterilization step (Step S16) of sterilizing the inside of the packaged medical device may be performed after the sealing step (Step S14). When performing the cutting step (Step S15), the interior sterilization step (Step S16) is preferably performed after the cutting step (Step S15). A sterilization method in the interior sterilization step is preferably radiation sterilization or electron beam sterilization.

In the manufacturing method of this embodiment, when the medical devices inside the container are fixed, a vacuum bag is not used and a lid member of a sheet shape covering the opening portion of the container is used. In the case of the method using the vacuum bag as in the conventional technique, it is necessary to open the vacuum bag and place the container in the vacuum bag. According to the conventional method, it is difficult to adjust the pressure in the opened vacuum bag to a desired value and the decompressed state in the vacuum bag becomes uneven depending on the air quantity in the vacuum bag or the position where the container is placed. Therefore, a problem that the fixed states of the medical devices vary arises in some cases. However, in the manufacturing method of this embodiment, the vacuum bag is not used, and therefore the problem does not arise and the fixed states of the medical devices are hard to vary.

Figure 6:
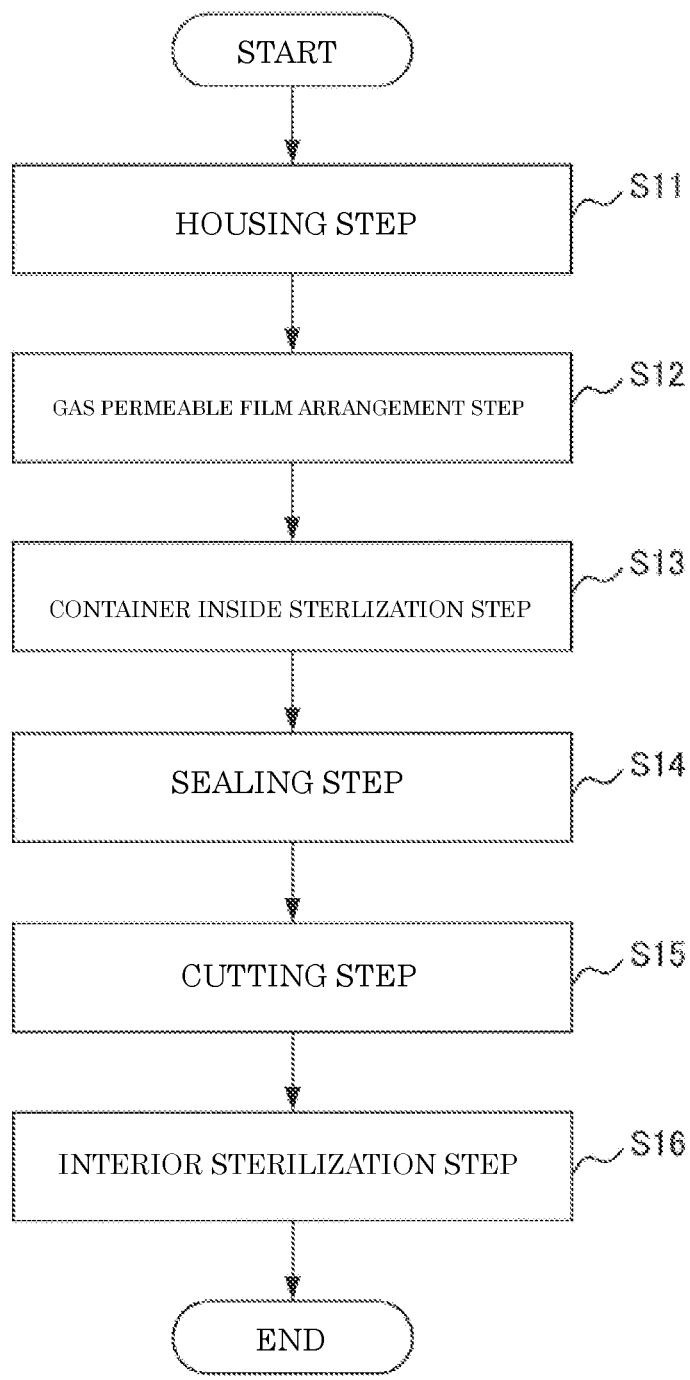
FIG. 6 is a flow chart illustrating an example of a method for manufacturing a packaged medical device.

Next, another embodiment of a method for manufacturing a packaged medical device is described with reference to FIG. 6. FIG. 6 is a flow chart illustrating an example of the method for manufacturing a packaged medical device. The manufacturing method of this embodiment may comprise, in addition to the steps illustrated in FIG. 5 described above, a gas permeable film arrangement step (Step S12) and a container inside sterilization step (Step S13). Hereinafter, points different from the embodiment illustrated in FIG. 5 are described.

In the manufacturing method of this embodiment, the gas permeable film arrangement step (Step S12) of disposing the gas permeable film in the opening portion of the container may be performed between the housing step (Step S11) and the sealing step (Step S14). In this step, the gas permeable film is placed on the medical devices or the holding portions inside the container and the gas permeable film is heat-sealed to the flange portion of the container, for example.

In the manufacturing method of this embodiment, the container inside sterilization step (Step S13) of sterilizing the inside of the container may be performed between the housing step (Step S11) and the sealing step (Step S14). When the gas permeable film arrangement step (Step S12) is performed, the container inside sterilization step (Step S13) is preferably performed between the gas permeable film arrangement step (Step S12) and the sealing step (Step S14). Thus, the degree of sanitation inside the container can be further increased. A sterilization method is not particularly limited and known sterilization methods, such as radiation sterilization, are usable and sterilization by gas or vapor is preferable. The interior sterilization step (Step S16) illustrated in FIG. 6 is not an indispensable step but an arbitrary step as described above. For example, in the case where the inside of the container is sufficiently sterilized by the container inside sterilization step (Step S13) or the like, the interior sterilization step (Step S16) may not be performed.

The present invention can also take the following aspects.

[1] A packaged medical device comprising:

a container having an opening portion and a flange portion formed to extend outward in a peripheral portion of the opening portion;

a medical device housed inside the container; and a lid member having a gas impermeable film and peelably heat-sealed to the flange portion, wherein an inside of the container is set to a negative pressure relative to an atmospheric pressure so that the medical device is pressed by the lid member, peel strength to the flange portion of the lid member is 2 to 50 N/in, the container comprises a holding portion holding the medical device inside the container, the container comprises a bottom surface portion, a side peripheral portion extending upward from the periphery of the bottom surface portion, and a projection portion projecting inward on the side peripheral portion, the holding portion is supported in the lateral direction of the container by the projection portion so as to suppress a horizontal movement of the holding portion, and the height of the projection portion is equal to the height of side peripheral portion of the container in which the opening portion and the flange portion are formed at a top end of the side peripheral portion.

[2] The packaged medical device according to [1], wherein a pressure inside the container is 400 to 1013 hPa.

[3] The packaged medical device according to [1], wherein the lid member is peelably heat-sealed to the flange portion through an adhesive or an adhesive layer configuring the lid member.

[4] The packaged medical device according to [3], wherein the adhesive or the adhesive layer configuring the lid member comprises an olefin-based resin.

[5] The packaged medical device according to [1], wherein the lid member is peelable from the flange portion by interfacial peeling or cohesive peeling.

[6] The packaged medical device according to [1], wherein the lid member comprises the gas impermeable film and a gas permeable film positioned on the container side relative to the gas impermeable film.

[7] A container comprising:

an opening portion and a flange portion formed to extend outward in a peripheral portion of the opening portion;

a medical device housed inside the container;

a holding portion holding the medical device inside the container; and a bottom surface portion, a side peripheral portion extending upward from the periphery of the bottom surface portion, and a projection portion projecting inward on the side peripheral portion, wherein the holding portion is supported in the lateral direction of the container by the projection portion so as to suppress a horizontal movement of the holding portion, and the height of the projection portion is equal to the height of side peripheral portion of the container in which the opening portion and the flange portion are formed at a top end of the side peripheral portion.

REFERENCE SIGNS LIST

1: packaged medical device
20: container
21: opening portion
22: bottom surface portion
23: side peripheral portion
24: flange portion
25: level difference portion
26: projection portion
30: medical device
40: lid member
50: holding portion
51: substrate portion
52: cylindrical portion
53: locking projection portion
54: through-hole
55: support portion
56: notch portion
57: connection hole
531: locking claw

What is claimed is:

1. A packaged medical device comprising:
a container having an opening portion and a flange portion formed to extend outward in a peripheral portion of the opening portion;
a medical device housed inside the container; and
a lid member having a gas impermeable film and peelably heat-sealed to the flange portion, wherein
an inside of the container is set to a negative pressure relative to an atmospheric pressure so that the medical device is pressed by the lid member,
peel strength to the flange portion of the lid member is 2 to 50 N/in,
the container comprises a holding portion holding the medical device inside the container,
the container comprises a bottom surface portion, a side peripheral portion extending upward from the periphery of the bottom surface portion, and a projection portion projecting inward on the side peripheral portion,
the holding portion is supported in the lateral direction of the container by the projection portion so as to suppress a horizontal movement of the holding portion, and
the height of the projection portion is equal to the height of side peripheral portion of the container in which the opening portion and the flange portion are formed at a top end of the side peripheral portion.

2. The packaged medical device according to claim 1, wherein a pressure inside the container is 400 to 1013 hPa.

3. The packaged medical device according to claim 1, wherein the lid member is peelably heat-sealed to the flange portion through an adhesive or an adhesive layer configuring the lid member.

4. The packaged medical device according to claim 3, wherein the adhesive or the adhesive layer configuring the lid member comprises an olefin-based resin.

5. The packaged medical device according to claim 1, wherein the lid member is peelable from the flange portion by interfacial peeling or cohesive peeling.

6. The packaged medical device according to claim 1, wherein the lid member comprises the gas impermeable film and a gas permeable film positioned on the container side relative to the gas impermeable film.

7. A container comprising:
an opening portion and a flange portion formed to extend outward in a peripheral portion of the opening portion;
a medical device housed inside the container;
a holding portion holding the medical device inside the container;
a bottom surface portion, and a side peripheral portion extending upward from the periphery of the bottom surface portion; and
a projection portion projecting inward on the side peripheral portion and the projection portion extending upward from a middle of the side peripheral portion with reference to a height between the bottom surface to a top end of the side peripheral portion,
wherein the holding portion is supported in the lateral direction of the container by the projection portion so as to suppress a horizontal movement of the holding portion, and
the height of the projection portion is equal to the height of side peripheral portion of the container in which the opening portion and the flange portion are formed at the top end of the side peripheral portion.

* * * * *